(12) United States Patent
Klingensmith et al.

(10) Patent No.: US 6,381,350 B1
(45) Date of Patent: Apr. 30, 2002

(54) INTRAVASCULAR ULTRASONIC ANALYSIS USING ACTIVE CONTOUR METHOD AND SYSTEM

(75) Inventors: Jon D. Klingensmith, Shaker Heights; David Geoffrey Vince, University Heights; Raj Shekhar, Mayfield Heights, all of OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/347,209

(22) Filed: Jul. 2, 1999

(51) Int. Cl.$^7$ .................................................. G06K 9/00
(52) U.S. Cl. ...................................... 382/128; 600/485
(58) Field of Search ........................ 382/128, 27, 256, 382/129, 130, 131, 132; 128/672, 922; 424/101; 600/443, 485

(56) References Cited

U.S. PATENT DOCUMENTS

| | | | | |
|---|---|---|---|---|
| 4,562,843 A | * | 1/1986 | Djordjevich et al. | 128/672 |
| 4,771,470 A | * | 9/1988 | Geiser et al. | 382/27 |
| 4,837,379 A | * | 6/1989 | Weinberg | 424/101 |
| 5,559,901 A | * | 9/1996 | Lobregt | 382/256 |
| 5,570,430 A | * | 10/1996 | Sheenhan et al. | 382/128 |
| 5,724,978 A | | 3/1998 | Tenhoff | |
| 5,752,522 A | | 5/1998 | Murphy | |
| 5,771,895 A | | 6/1998 | Slager | |
| 5,830,145 A | | 11/1998 | Tenhoff | |
| 5,885,218 A | * | 3/1999 | Teo et al. | 600/443 |
| 6,053,869 A | * | 4/2000 | Kawagishi et al. | 600/443 |

OTHER PUBLICATIONS

A Fast Algorithm for Active Contours—Donna J. Williams and Mubarak Shah, IEEE 1990.
A Fast Algorithm for Active Contours and Curvature Estimation—Donna J. Williams and Mubarak Shah, CVGIP: Image Understanding, vol. 55, No. 1, Jan. 1996.

* cited by examiner

*Primary Examiner*—Bhavesh Mehta
*Assistant Examiner*—Abol Pazl Tabatabai
(74) *Attorney, Agent, or Firm*—Calfee, Halter & Griswold LLP

(57) ABSTRACT

An intravascular ultrasound (IVUS) analysis system and method is provided which determines luminal and medial-adventitial boundaries of a blood vessel. Ultrasonic data is acquired by a rotating transducer mounted to a tip of a catheter which is inserted into the blood vessel. An intravascular image is reconstructed from the ultrasound data. To determine the luminal boundary of a vessel, a user selects boundary points on the image believed to be locations of the luminal boundary. A boundary contour is generated based on the boundary points. The boundary contour is then optimized by adjusting the boundary points based on a radially determined edge of the luminal boundary performed on the image in polar format. Once the final luminal boundary contour is generated, the process is repeated to determine the medial-adventitial boundary contour. With the contour data, properties of the blood vessel are analyzed including determining the area of the lumen and percent of occlusion caused by plaque.

27 Claims, 11 Drawing Sheets

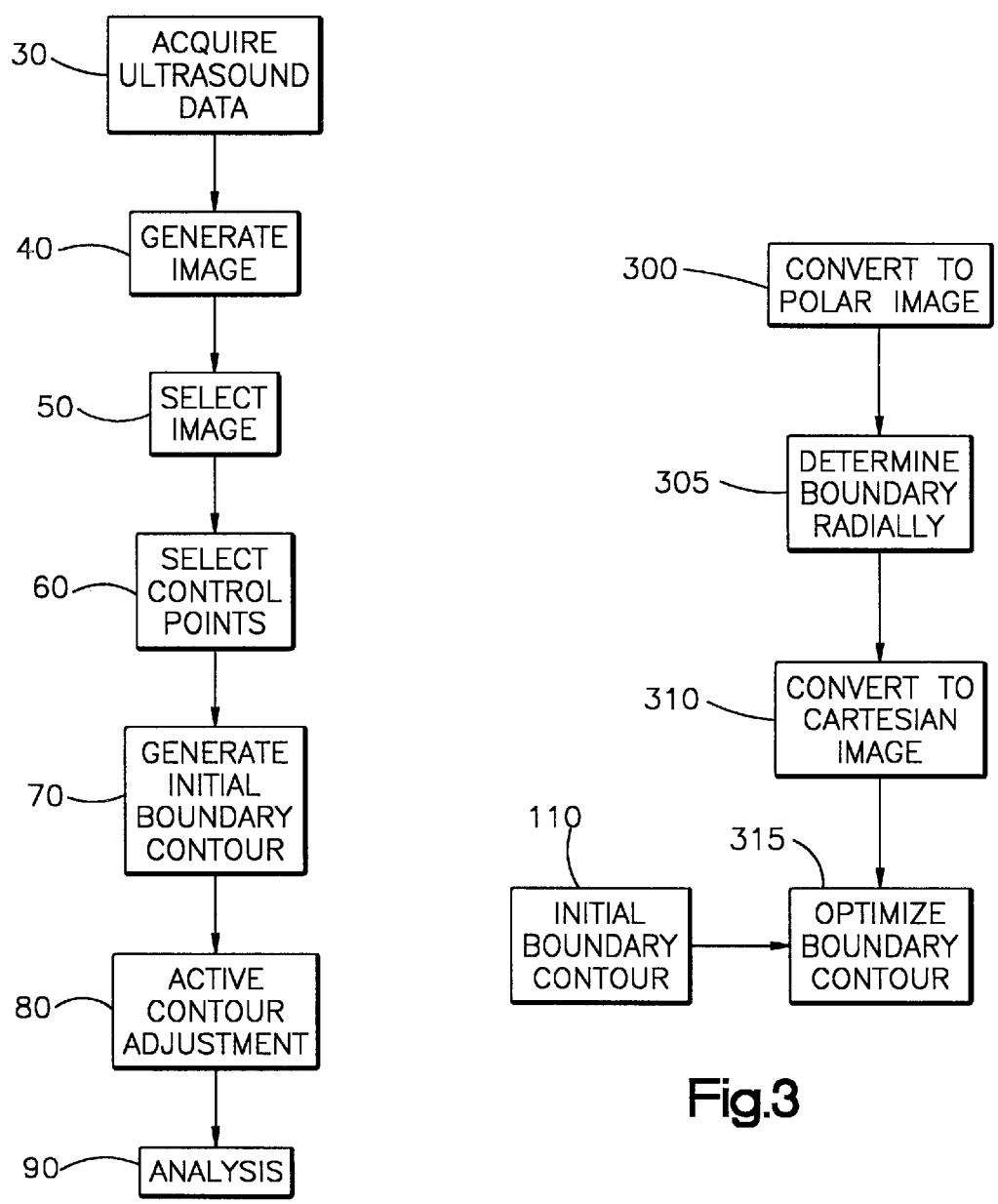

700 710 720 725
705 715

730
705
715
725

INTRAVASCULAR ULTRASONIC ANALYSIS USING ACTIVE CONTOUR METHOD AND SYSTEM

BACKGROUND OF THE INVENTION

The present invention relates to medical imaging arts. It finds particular application to an intravascular ultrasonic image analysis method and system which determines luminal and medial-adventitial boundaries of a vascular object.

Ultrasonic imaging of portions of a patient's body provides a useful tool in various areas of medical practice for determining the best type and course of treatment. Imaging of the coronary vessels of a patient by ultrasonic techniques can provide physicians with valuable information. For example, the image data may show the extent of a stenosis in a patient, reveal progression of disease, help determine whether procedures such as angioplasty or atherectomy are indicated or whether more invasive procedures may be warranted.

In a typical ultrasound imaging system, an ultrasonic transducer is attached to the end of a catheter that is carefully maneuvered through a patient's body to a point of interest such as within a blood vessel. The transducer is a single-element crystal or probe which is mechanically scanned or rotated back and forth to cover a sector over a selected angular range. Acoustic signals are transmitted during the scanning and echoes from these acoustic signals are received to provide data representative of the density of tissue over the sector. As the probe is swept through the sector, many acoustic lines are processed building up a sector-shaped image of the patient.

After the data is collected, images of the blood vessel are reconstructed using well-known techniques. Since the data is acquired along a section of the vessel, hundreds of intravascular images may be generated. A typical analysis includes determining the size of the lumen and amount of plaque in the vessel. This is performed by having a user visually analyze each image and manually draw a boundary contour on the image at a location where the user believes is the luminal boundary and medial-adventitial boundary of the vessel. This is a very time consuming process which can take days to evaluate a set of images from one patient. Furthermore, the boundary determination is made more difficult when the images are of poor quality and the boundaries are difficult to see on the image.

The present invention provides a new and unique intravascular ultrasonic image analysis method and system with cures the above problems and others.

SUMMARY OF THE INVENTION

In accordance with the present invention, a new and unique method for determining a boundary contour of a blood vessel is provided. An intravascular ultrasound image of the blood vessel is generated from data acquired radially within the blood vessel by an ultrasonic device. The ultrasound image is displayed to a user where the image includes a representation of a boundary of the blood vessel. The user selects control points along the boundary. The control points are interpolated to generate a boundary contour. The boundary contour is then optimized by adjusting each of the control points based on a gradient image which includes a distinguished boundary determined from the ultrasound image.

In accordance with a more limited aspect of the present invention, the distinguished boundary is determined by radially analyzing pixel values of the ultrasound image.

In accordance with a more limited aspect of the present invention, the gradient image is formed by converting the ultrasound image to a polar image where the polar image has a plurality of radial scan lines which include a plurality of pixels. An edge of the boundary is radially determined along each of the radial scan lines by applying a gradient filter to each of the plurality of pixels. The gradient filter distinguishes pixels which likely form the edge of the boundary. The distinguished pixels defme the distinguished boundary.

In accordance with another aspect of the present invention, a method of intravascular analysis of an intravascular image is provided. The intravascular image is generated from data acquired by an ultrasonic device which radially scans a vascular object internally. The intravascular image is converted to a Cartesian format which includes a representation of a boundary of the vascular object. Boundary points are selected on the intravascular image in a vicinity of the boundary. A first boundary contour is generated based on the boundary points. A second boundary contour is then generated based on radial boundary determined performed on a polar image of a intravascular image. The first boundary contour is then adjusted by an influence from the second boundary contour to obtain an optimized boundary contour.

In accordance with a more limited aspect of the present invention, the radial boundary determination includes applying a gradient filter in a radial direction on the polar image. The gradient filter distinguishes areas of the polar image in the vicinity of the boundary of the vascular object.

One advantage of the present invention includes determining luminal and medial-adventitial boundaries from an ultrasound image using image data having the same format as the IVUS data which was collected. In particular, IVUS data is collected radially by a rotating transducer or array of transducers. Thus, to obtain a more accurate boundary determination, the boundary determination is influenced by radial edge detection from a polar format of an image.

Another advantage of the present invention is that the determination of luminal and medial-adventitial boundaries is accurately performed. Additionally, the present system reduces the time necessary for a user to determine these boundaries which may involve manually processing hundreds of images.

Another advantage of the present invention is that boundary determination can be performed in real-time, for example, in an operating room. In this manner, a surgeon can receive immediate data relating to a patient's blood vessels.

Still further advantages of the present invention will become apparent to those of ordinary skill in the art upon reading and understanding the following detailed description of the preferred embodiments.

BRIEF DESCRIPTION OF THE DRAWINGS

The following is a brief description of each drawing used to describe the present invention, and thus, are being presented for illustrative purposes only and should not be imitative of the scope of the present invention, wherein:

FIG. 1 is a block diagram of an overall ultrasonic imaging system;

FIG. 2 is a process diagram of acquiring and analyzing ultrasound data in accordance with the present invention;

FIG. 3 is a block diagram of optimizing a boundary contour based on a radially determined boundary in accordance with the present invention;

DETAILED DESCRIPTION OF THE PREFERRED EMBODIMENTS

With reference to FIG. 1, an overall intravascular ultrasound (IVUS) system is shown. An IVUS system console 10 collects ultrasonic data from a transducer (not shown). The transducer is attached to the end of a catheter that is carefully maneuvered through a patient's body to a point of interest. In the present system, the catheter is maneuvered through the interior of vascular organs in order to obtain intravascular ultrasound data of the surrounding vascular tissue. The IVUS system console 10 is, for example, a C-VIS Clearview Imaging System and the transducer is a single element mechanically rotated ultrasonic device having at least a frequency of 20 MHz. The ultrasonic device may also be an array of transducers circumferentially positioned to cover 360° where each transducer radially acquires data from a fixed position.

Figure 6A:
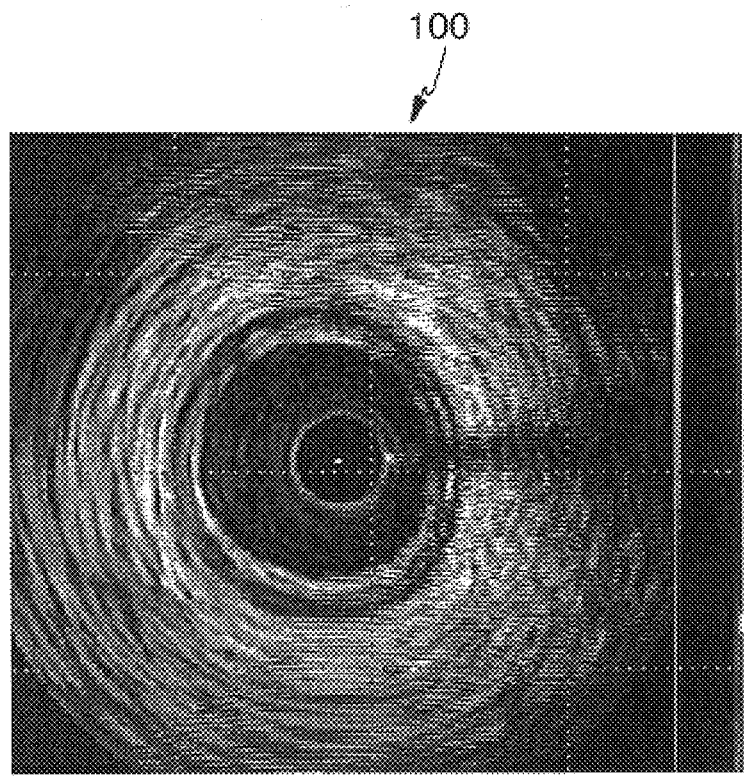
FIG. 6A is the intravascular image in Cartesian format.

An exemplary process for collecting ultrasound data is as follows. Once the transducer reaches a desired point within the vascular object, the transducer is pulsed and then acquires echoes for about 7 micro seconds. It is rotated 1.5 degrees and pulsed again. This is repeated for 240 scan lines around 360 degrees. The number of samples acquired in each scan line controls the depth of the echoes recorded by the transducer and ultimately the resolution of the image. An image reconstruction processor 15 reconstructs an image from the raw ultrasound data. The reconstruction is performed using any image reconstruction routine known to those of ordinary skill in the art. The present application is not directed to image reconstruction and, thus, will not be discussed in detail. An exemplary reconstructed ultrasound image is shown in FIG. 6A which shows a cross-sectional view of a blood vessel.

The ultrasound data is collected radially by the rotating transducer. The rotational position of the transducer at each point in time a scan line is acquired is used to create the image. Thus, the data is in polar format where each data has an angle θ and a radius R associated with it. Polar images are, however, difficult for a user to visually interpret so the polar data is converted to x and y Cartesian image coordinates. This process is called scan conversion. Equations (1) and (2) show the common polar to Cartesian coordinate transformation.

$$X = R \cdot \cos(\theta) \quad (1)$$

$$Y = R \cdot \sin(\theta) \quad (2)$$

Scan conversion is well known in the art and is performed by looping through the polar image, calculating the corresponding Cartesian location from R and θ using bi-linear interpolation of neighboring pixels, and assigning the pixel value at the polar location to the Cartesian location. Once the image data is generated, an image analysis routine 20 analyzes the image data which is described in detail below.

With reference to FIG. 2, a block diagram of the IVUS image analysis process is shown. As explained above, ultrasound data is acquired 30 by the IVUS system console 10 where the data is acquired radially within a vascular object by an ultrasonic device. An intravascular image is generated 40 from the ultrasound data using any known image reconstruction process. A typical scan may generate hundreds of images along a section of the vascular object. The image data is originally in polar coordinates since the data is acquired radially and is then converted to a Cartesian format. A cross-sectional view of an intravascular image in Cartesian format is shown in FIG. 6A.

Figure 4:
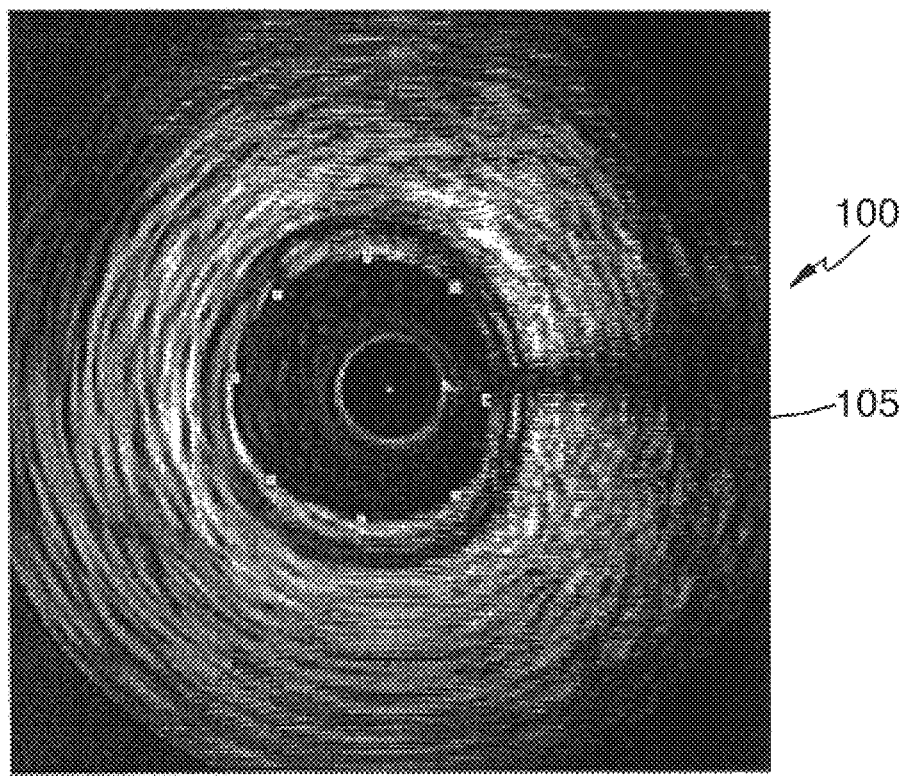
FIG. 4 is an intravascular ultrasound image showing selected boundary points in the vicinity of the luminal boundary.

Once the images are generated, a user may select one or more images for analysis and evaluation. In the preferred embodiment, an intravascular image is analyzed to determine a luminal boundary and a medial adventitial boundary of the vascular object which is imaged. With further reference to FIG. 2 and FIG. 4, an intravascular image 100 is selected and displayed 50 to the user. It is presumed that the user/operator is experienced in reading ultrasonic images and visually determining an approximate location of the luminal boundary and medial-adventitial boundary. The user selects 60 a set of boundary control points 105 at locations on the image where the user believes are the edges of a boundary, in this case, a luminal boundary.

Figure 5:
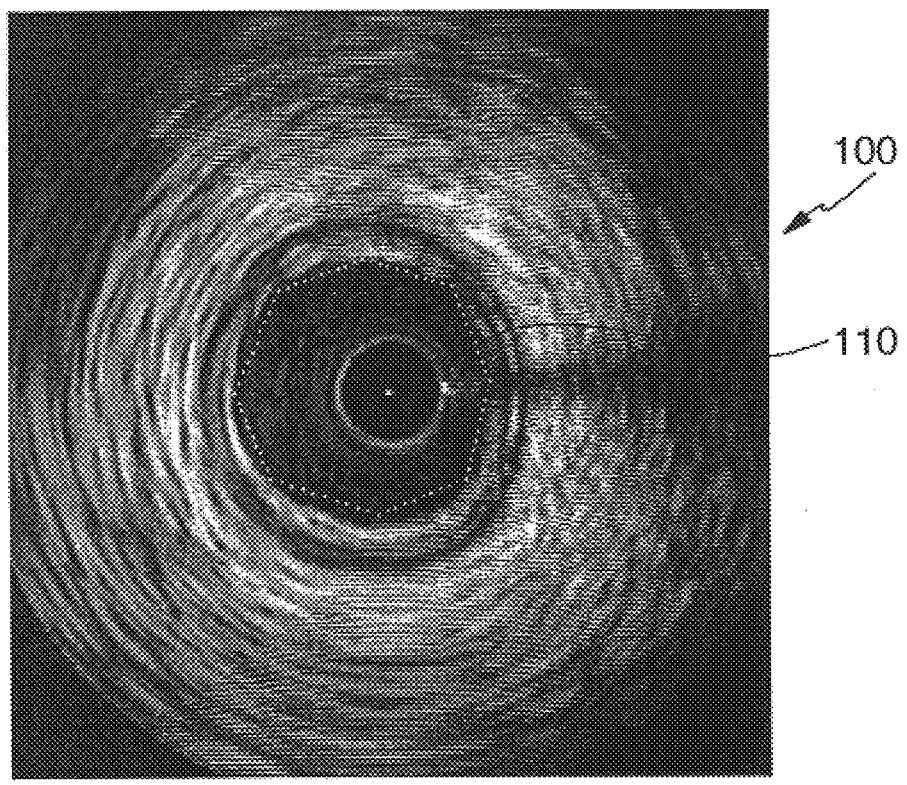
FIG. 5 shows an initial boundary contour generated from the boundary points of FIG. 4.

With reference to FIG. 5, an initial boundary contour 110 is generated 70 based on the selected control points 105. The initial contour 110 connects the control points resulting in an approximate location of the boundary edge. Additional control points may be automatically generated by the system between the user selected control points 105 to generated a better approximation of a boundary edge. The initial boundary 110 can be obtained by interpolating between the control points 105.

With further reference 2, after the initial boundary contour 110 is generated, an active contour adjustment 80 is performed to obtain an optimized boundary contour which is close to or on the actual boundary edge of interest. In general, the active contour adjustment 80 takes the initial contour 110, which is a roughly defined contour close to the edge of interest, and moves it around within the image data under an influence of several forces, external and/or internal, until it finds the edge of interest. The external forces are derived from image data properties such that the initial contour 110 is adjusted towards the nearest edge in the image data. The internal forces are defined such that they are proportional to the curvature of the initial contour 110, and restricts contour adjustment such that the contour maintains first and second order continuity. In the preferred embodiment, the active contour adjustment 80 is based on minimizing an energy functional of Equation (3):

$$E = \int (\alpha(s) \cdot E_{cont} + \beta(s) \cdot E_{curv,t} + \beta_L(S) \cdot E_{curv,L} + \gamma(S) \cdot E_{image}) ds \quad (3)$$

The first term $E_{cont}$ controls the first order of continuity and the second term $E_{curv}$ controls second order continuity. The last term $E_{image}$ is based on an image quantity determined from the image data. In the preferred embodiment, the image quantity is edge strength based on pixel values in the image. Of course, other terms which control external constraints can be included in the functional to obtain a desired result. The parameters $\alpha$, $\beta$, and $\gamma$ are weighting factors which control the relative input between the terms. The value of a weighing factor can be increased to increase its influence on the functional. For example, by increasing the value of $\gamma$, and decreasing the values of $\alpha$, and $\alpha$, the contour adjustment can be made to be entirely influenced by the $E_{image}$ term.

Each control point 105 corresponds to a vertex on the initial contour 110 which resides at a pixel location on the intravascular image 100. To improve the contour, neighborhood locations of each vertex (control point) are searched and a location in the neighborhood giving the smallest value for the functional is chosen as the new location for the vertex (control point). This process is repeated through all control points until the number of points moved is less than a specified threshhold or a user defined maximum number of iterations is reached.

Looking to the functional, the first term $E_{count}$ is formed by taking an average distance between all contour vertices and subtracting the distance between the current vertex and the previous vertex location as shown by the following Equation:

$$E_{cont} = d - |v_i - v_{i-1}| \quad (4)$$

In the above Equation, the $v_i$ denotes the $i^{th}$ vertex and d is the average distance between all the control points 105. This expression eliminates the possibility of the contour's curve shrinking while satisfying a first order continuity by encouraging even spacing between control points. Points having a distance between them which is near the average distance produce a small value for $E_{count}$. A goal of the functional is finding minimum values. The average distance d between the points is then recalculated on every interation.

The second term $E_{curv}$ encourages second order of continuity and is a curvature term. An estimate of the curvature is shown in the following Equation:

$$E_{curv} = |v_{i-1} - 2v_i + v_{i+1}|^2 \quad (5)$$

Small values of $E_{curv}$ in this expression encourage the reduction of curvature which helps the contour 110 maintain its shape and prevents formation of corners. If corners, or other shape features are desired in the final result, the weighing factor $\beta$ can be adjusted accordingly to raise or lower the influence of curvature in the functional minimization.

External forces acting on the contour 110 are represented in the third term $E_{image}$ of the functional. The definition of the third term controls what image features or properties the contour 110 is attracted to. In the preferred embodiment, $E_{image}$ is based on gradient values in the image. As explained previously, the ultrasound data is acquired radially by a transducer and, thus, the data is polar in nature. Therefore, to obtain more accurate gradient values of the image to influence the adjustment of the boundary contour 110, the gradient values are determined from a polar image of the intravascular image 100.

With reference to FIGS. 6A–B and 7A–B, formation of a gradient image which is used to optimize the boundary contour is shown. The original intravascular image 100 selected by the user is shown in FIG. 6A. The initial boundary contour 110 is generated from this image shown in FIGS. 4 and 5.

Figure 6B:
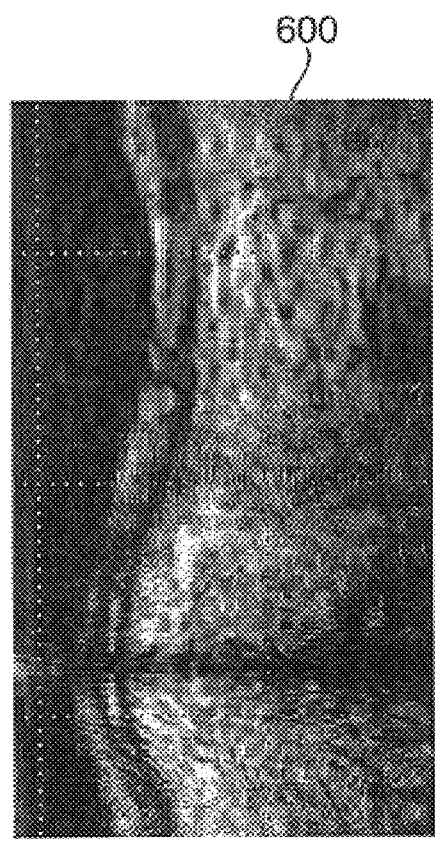
FIG. 6B is the image in FIG. 6A in polar format.

With reference to FIG. 3, a process for generating the gradient image and optimizing the boundary contour 110 is illustrated. The intravascular image 100 is shown in Cartesian format in FIG. 6A and is converted 300 to a polar image 600 as shown in FIG. 6B. As explained above, the image features which will influence the adjustment of the boundary contour 110 are the gradient values of the polar image 600. The polar image 600 includes a plurality of radial scan lines (not shown) which are defined horizontally across FIG. 6B as is known in the art. Each scan line contains a plurality of pixel values where each pixel value represents a number, for example between 0 and 255 for an 8-bit system, where 0 represents black and 255 represents white. Once the polar image is generated, the boundaries of the vascular object are determined 305 radially along each scan line. In the preferred embodiment, the boundary determination is performed by applying a one-dimensional gradient filter across each scan line where the filter is: [−6, −4, −2, 0, 2, 4, 6]. The filter is applied to the pixels of each scan line in a radial direction and filtered gradient pixel values are found by:

$$\text{Pixel Value } D = (-6A) + (-4B) + (-2C) + (0D) + (2E) + (4F) + (6G) \quad (6)$$

Where the alphabetical letters A–G represent a gray value for a pixel. The current pixel is D and its new gradient value is determined based on the values of three previous pixels A, B and C and three subsequent values E, F and G in the radial direction along the current scan line. Of course, there are many gradient filters known in the art which can be used to radially determine edges in an image. By applying the gradient filter, the pixel values of the image near an edge become a distinguished gradient value from other values in the image.

Figure 7A:
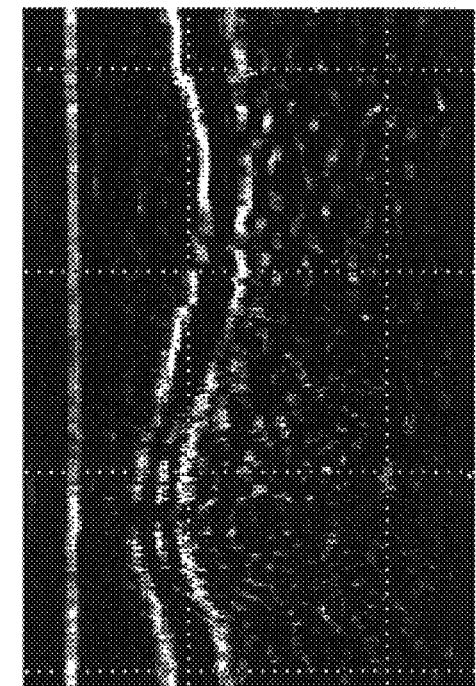
FIG. 7A illustrates the image of FIG. 6B as a gradient image after filtering.
Figure 7B:
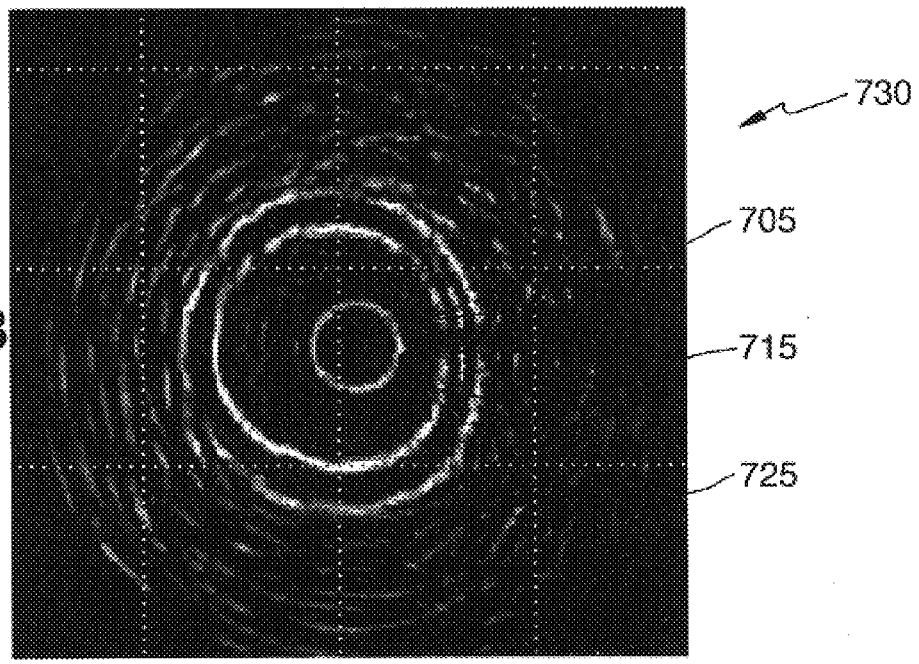
FIG. 7B is the gradient image of FIG. 7A scan converted into Cartesian format.

With reference to FIG. 7A, a gradient image is shown which is a result of applying the gradient filter to the polar image 600 of FIG. 6B. Area 700 represents the catheter which was inserted into the blood vessel and 705 is the edge of the catheter 700. Area 710 represents the lumen of the blood vessel and boundary 715 is the luminal boundary. The medial-adventital boundary of the blood vessel is represented by 725. Area 720, which lies between the luminal boundary 715 and the medial-adventitial boundary 725, may represent the build up of plaque in the blood vessel. The polar gradient image is then converted 310 to a Cartesian format gradient image 730 shown in FIG. 7B. The conversion puts the gradient image 730 into the same format as the intravascular image 100 containing the initial boundary contour 110 an optimized boundary contour 315.

Gradient values of the gradient image 730 are used to calculate the $E_{image}$ term for the minimization and contour adjustment. The boundary contour 110 is optimized 315 based on the edge boundaries found in the gradient image 730. The $E_{image}$ term is found by:

$$E_{image} = \frac{(\min - g)}{(\max - \min)} \quad (7)$$

Optimizing the initial boundary contour 110 includes evaluating pixels neighboring each control point 105 to determine if the current control point is to be moved to a neighboring pixel.

Figure 8:
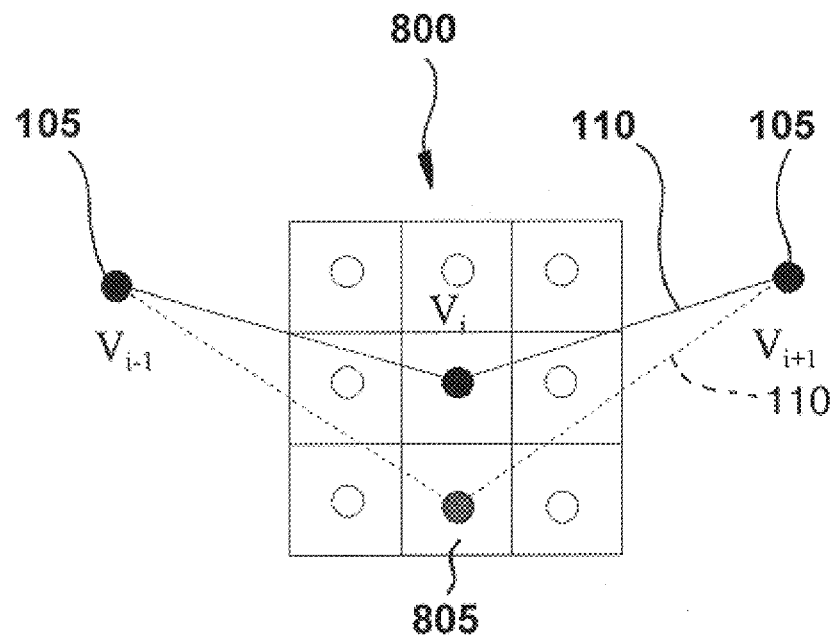
FIG. 8 is an illustration of moving contour vertices in a neighborhood of pixels in accordance with the present invention.

With reference to FIG. 8, an illustration of a neighborhood approach of moving boundary contour vertices is shown. A current boundary control point 105 is represented by vertex $V_i$ and its two adjacent control points are represented by $V_{i-1}$ and $V_{i+1}$. A pixel neighborhood 800 is illustrated with the pixel locations adjacent the $V_i$. The x,y location of the current control point in the intravascular image 100 is used as the location of $V_i$ in the gradient image 730 and identifies the neighborhood pixels 800. For each vertex V and its neighborhood 800, the $E_{image}$ term is calculated by determining the minimum and maximum gradient values in the neighborhood 800 which are the min and max terms of the equation. The gradient value at the vertex $V_i$ location is represented by g. The location in the neighborhood 800 which produces the minimum $E_{image}$ value, such as a negative value, means that it is a large gradient value. Large gradient values are typically those which are on or near the boundary edge. Thus, the contour will be attracted to edges with strong energy. For example, after the calculation, vertex $V_i$ might be moved to pixel location 805. With equation (1), the energy E is calculated for each position in the neighborhood 800 and the current vertex $V_i$ is moved to the position giving the minimum value. In this manner, the vertices of the boundary contour 110 move within the image data. The influential factor for adjusting the boundary contour 110 (shown in FIG. 5) is the boundary contour 715 shown in FIG. 7B which is a radially determined edge of the luminal boundary. A final optimized contour is obtained when the iteration process is complete.

Figure 9:
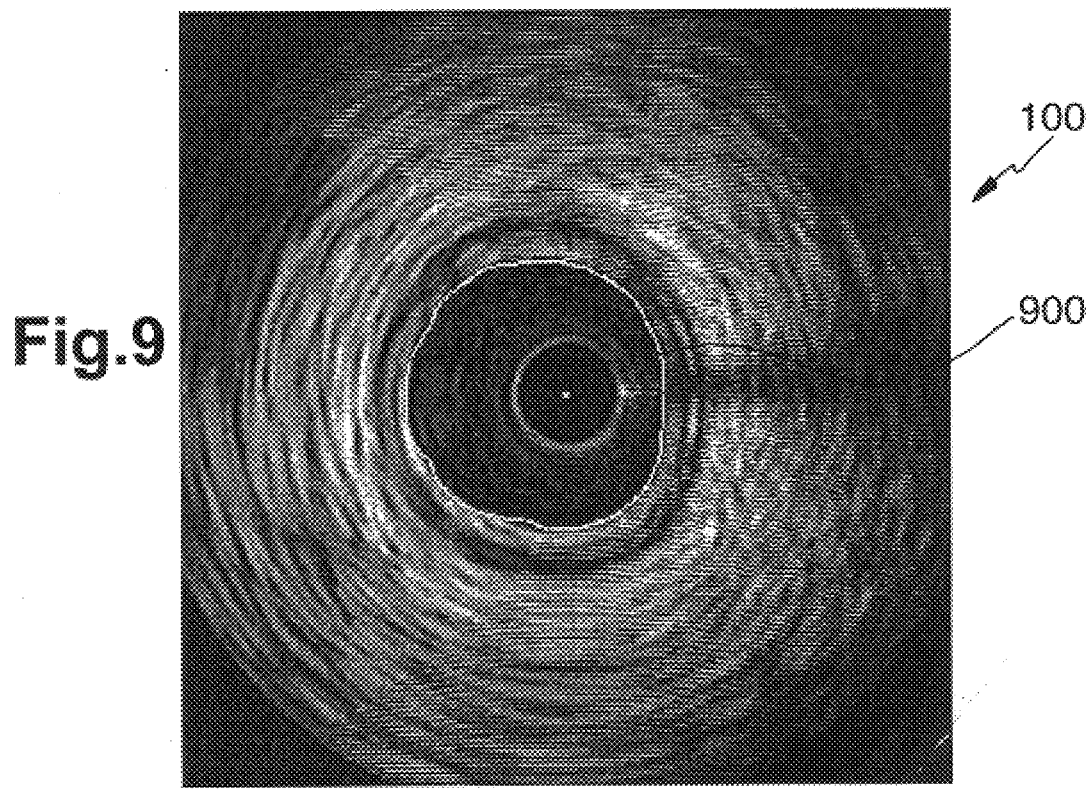
FIG. 9 shows the intravascular image of FIG. 5 with a final boundary contour in accordance with the present invention.

With reference to FIG. 9, a final luminal boundary contour 900 is overlaid on the original image 100 for the user to visualize. The final contour 900 is the result of optimizing the initial boundary contour 110. The process is then repeated to determine the medial-adventitial boundary of the blood vessel. In this process, the user selects a set of boundary points in the vicinity of the medial-adventitial boundary. A contour is generated and optimized as described. However, the distinguished boundary contour 725 shown in FIG. 7B (the outer circular boundary) is used to influence the active contour adjustment 80 rather than luminal boundary 715. As explained above, boundary 725 is a distinguished contour that is radially determined from the polar image 600 using a gradient filter.

Figure 10:
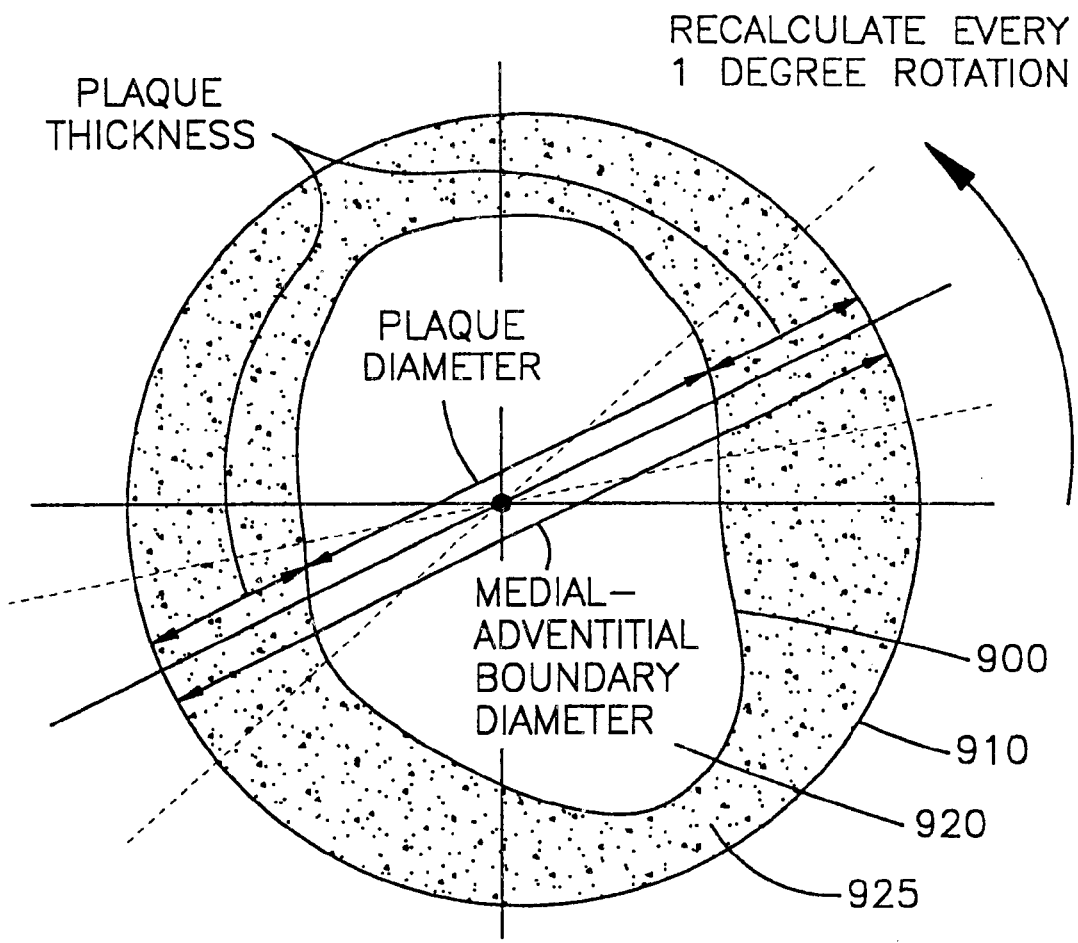
FIG. 10 is a representation of a blood vessel showing its luminal size and plaque thickness.

With reference to FIG. 10, a cross-sectional view representing a blood vessel illustrates an exemplary final luminal boundary 900 and a final medial-adventitial boundary 910. After these boundaries are determined with the present system, an analysis 90 of the blood vessel is performed. Such analysis includes determining the size of the lumen 920 and determining the thickness of plaque 925 shown between the luminal boundary 900 and the medial-adventitial boundary 910. Additionally, lumen/medial-adventitial boundary metrics are determined including cross-sectional area, centroid, maximum diameter, minimum diameter, and eccentricity. Furthermore, plaque metrics of the vessel are determined including cross-sectional area, maximum thickness, minimum thickness, eccentricity, and percent occlusion.

The present invention provides the ability to diagnose a blood vessel in real-time. For example, IVUS image data can be collected from a patient and images reconstructed. A user, who is in the operating room, can perform the present boundary determination for a selected section of images. A physician can receive, in real-time, an analysis of the vessel which returns the size of the lumen, percent occlusion, and other information about the vessel. Based on the analysis, the physician can immediately determine the size of a necessary stent or balloon, evaluate the progression of disease, or identify changes in vessel size which may require medical attention.

Figure 11:
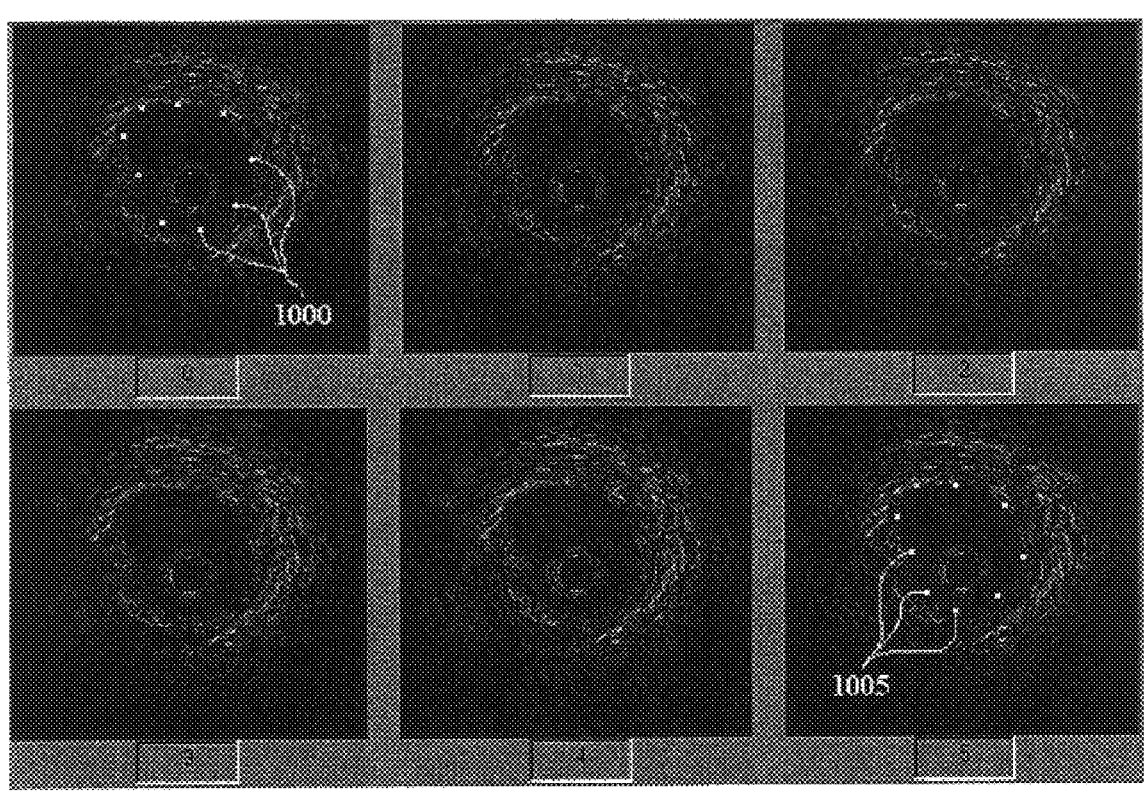
FIG. 11 shows a sequence of image frames where control points are selected on a starting and ending frame.

With reference to FIG. 11, the present invention generates a three-dimensional surface contour from a set of intravascular ultrasound images. Six sequential image slices or frames 0–5 are shown. It is to be understood that these six exemplary frames are part of a large set of frames which may include hundreds of images obtained during an ultrasonic scan. To determine a three-dimensional surface contour of the lumen of the vessel, the user selects a starting frame and an ending frame from a series of sequential image frames in order to generate an initial contour model. In this case, frame 0 is selected as the starting frame and frame 5 as the ending frame. Starting and ending frames are selected based on the visual similarity of the luminal boundary in the sequence of frames. In other words, the starting frame, ending frame and intermediate frames 1–4 therebetween each have a similar luminal contour. A frame which shows a substantially different luminal contour would not be included within a selected starting and ending frame group.

Figure 12:
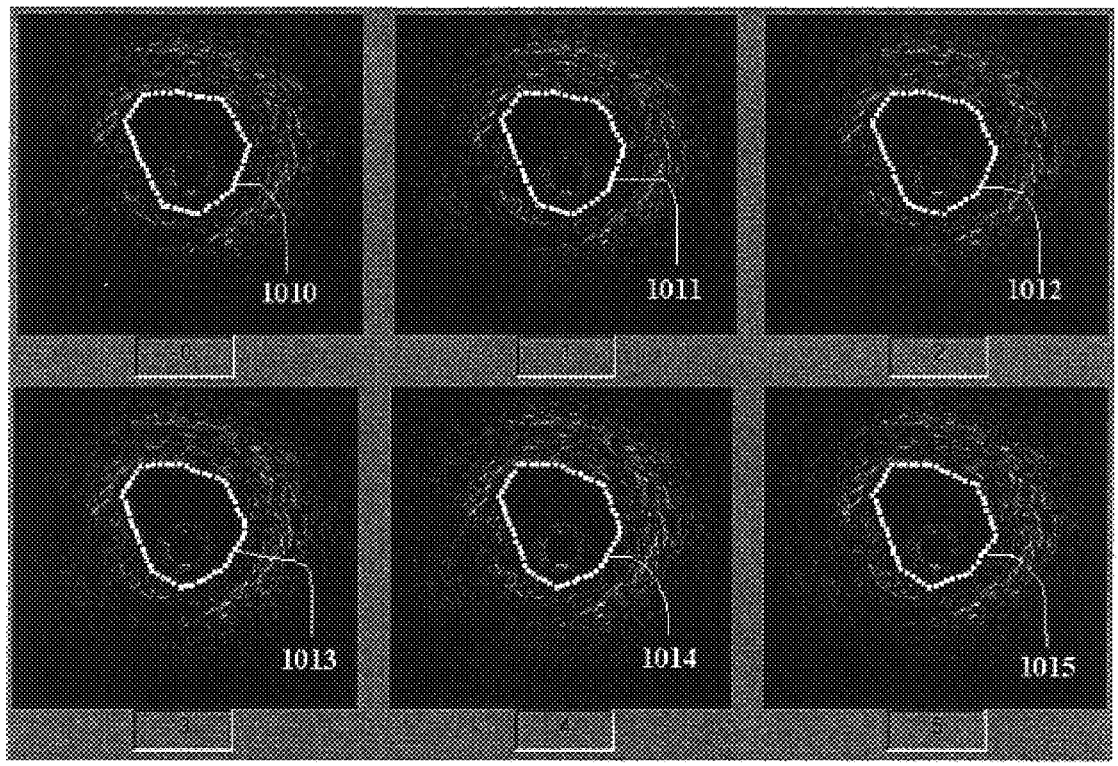
FIG. 12 shows the sequence of images frames including an initial luminal boundary contour for each frame.

With further reference to FIG. 11, the user selects a set of starting control points 1000 in the vicinity of the luminal boundary in the starting frame 0. The points are selected at locations where the user believes is the boundary. A set of end control points 1005 are similarly selected on the ending frame 5. The control points are then interpolated to generate a starting initial contour 1010 and an ending initial contour 1015 as shown in FIG. 12. Based on the starting and ending initial contours, a contour is automatically generated for each intermediate frame 1–4 designated as contours 1011–1014, respectively. For example, the intermediate contours can be generated by interpolating between the initial contours of the starting frame 0 and ending frame 5. Once initial luminal boundary contours are determined, they define three-dimensional surface data for the lumen within the segment of the vessel corresponding to the frames 0–5.

Figure 13:
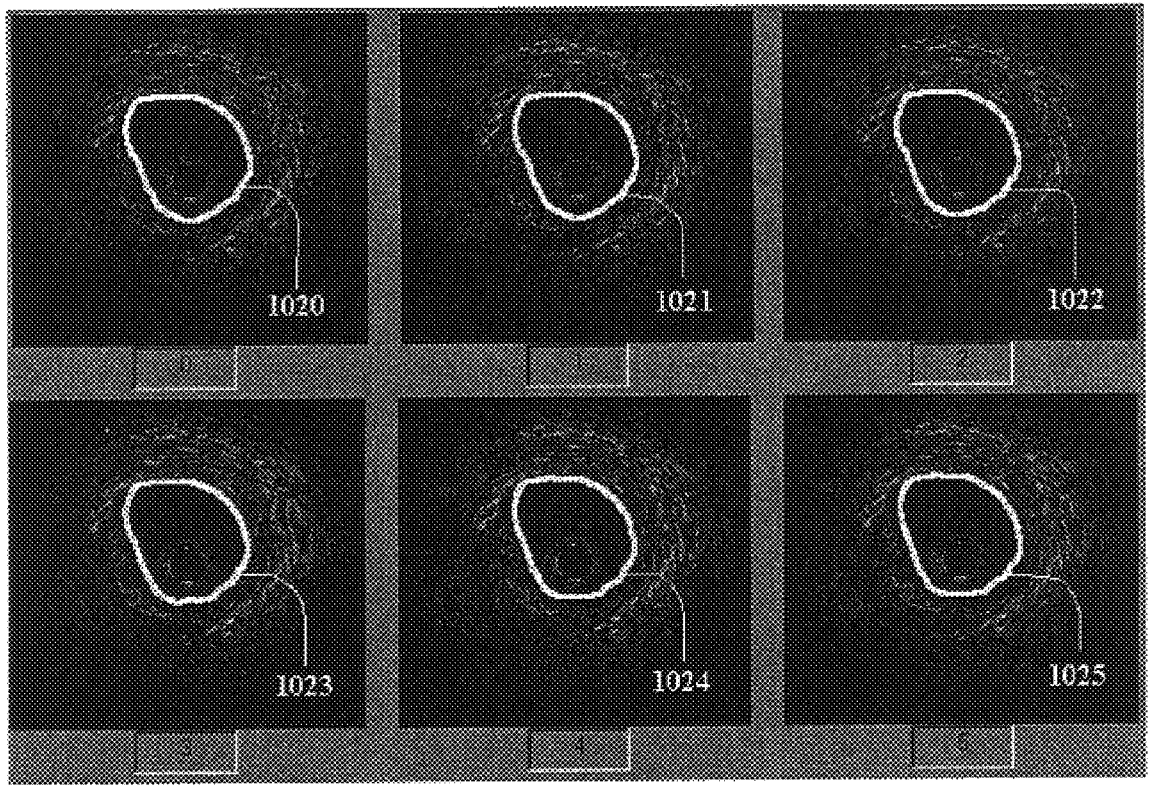
FIG. 13 shows the sequence of images frames including an optimized luminal boundary contour for each frame.

With reference to FIG. 13, the initial contours 1010–1015 shown in FIG. 12 are optimized according to the active contour method described above. The energy equation E, however, includes an additional $E_{curv}$ term as follows:

$$E=\int(\alpha(s)\cdot E_{cont}+\beta_T(s)\cdot E_{curv,T}+\beta_L(S)\cdot E_{curv,L}+\gamma(s)\cdot E_{image})ds \qquad (8)$$

Since the boundary contours are in three-dimensions, the curvature term now includes $E_{curv,T}$ which is a transverse curvature constraint and $E_{curv,L}$ which is a longitudinal curvature constraint. These terms limit the movement of points such that longitudinal continuity is maintained and kinks in the contour are prevented. The calculation of the term is similar, as explained above, except that the control vertices V are different. In the three-dimensional model, $V_i$ is a vertex from the current image frame, $V_{i-1}$ is the vertex from the previous frame and $V_{i+1}$ is the vertex from the next frame. Thus, bi-directional image data from adjacent frames is used to optimize the boundary contours.

The contour adjustment is performed iteratively, as described above, where the energy equation is calculated for each boundary control point on the initial contour 1010 of frame 0 one time through. The processing then moves to the next frame 1. After the ending frame 5 is optimized with the one iteration through all its control points, the process repeats with the starting frame 0 and continues to cycle through the frames until a user selected threshold condition is satisfied for the energy equation or, a user selected number of iterations are performed. As explained previously, the object of the energy equation is to minimize its values by adjusting each point on the contour towards the edge of the luminal boundary. The final contours in each frame become an optimized representation of the actual boundary contour of the lumen. Final optimized boundary contours 1020–1025 are shown in FIG. 13 as contours 1020–1025 in frames 0–5, respectively.

Figure 14:
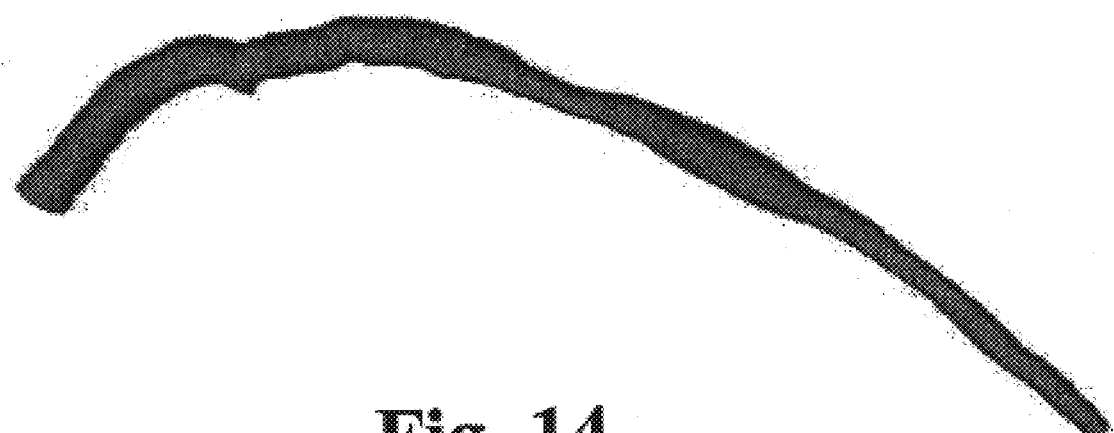
FIG. 14 shows a three-dimensional surface contour of a lumen as determined from optimized luminal boundary contour data in accordance with the present invention.

With reference to FIG. 14, a three-dimensional surface contour of a lumen of a blood vessel is shown as determined from a set of final optimized contours obtained from the present invention. The surface data is correlated by using the boundary contour data from one frame to the next. The present invention simplifies boundary determination for the user since input from the user is only required on a starting and ending image frame. Boundaries on intermediate image frames are automatically determined. Thus, hundreds of image frames can be quickly processed by the user by selective grouping of frames between starting and ending frames. Exemplary test results show that with the present invention, contours were determined for about 180 image frames in about 20 minutes. In contrast, a user typically needs about one hour to manually trace contours on ten images.

Figure 15:
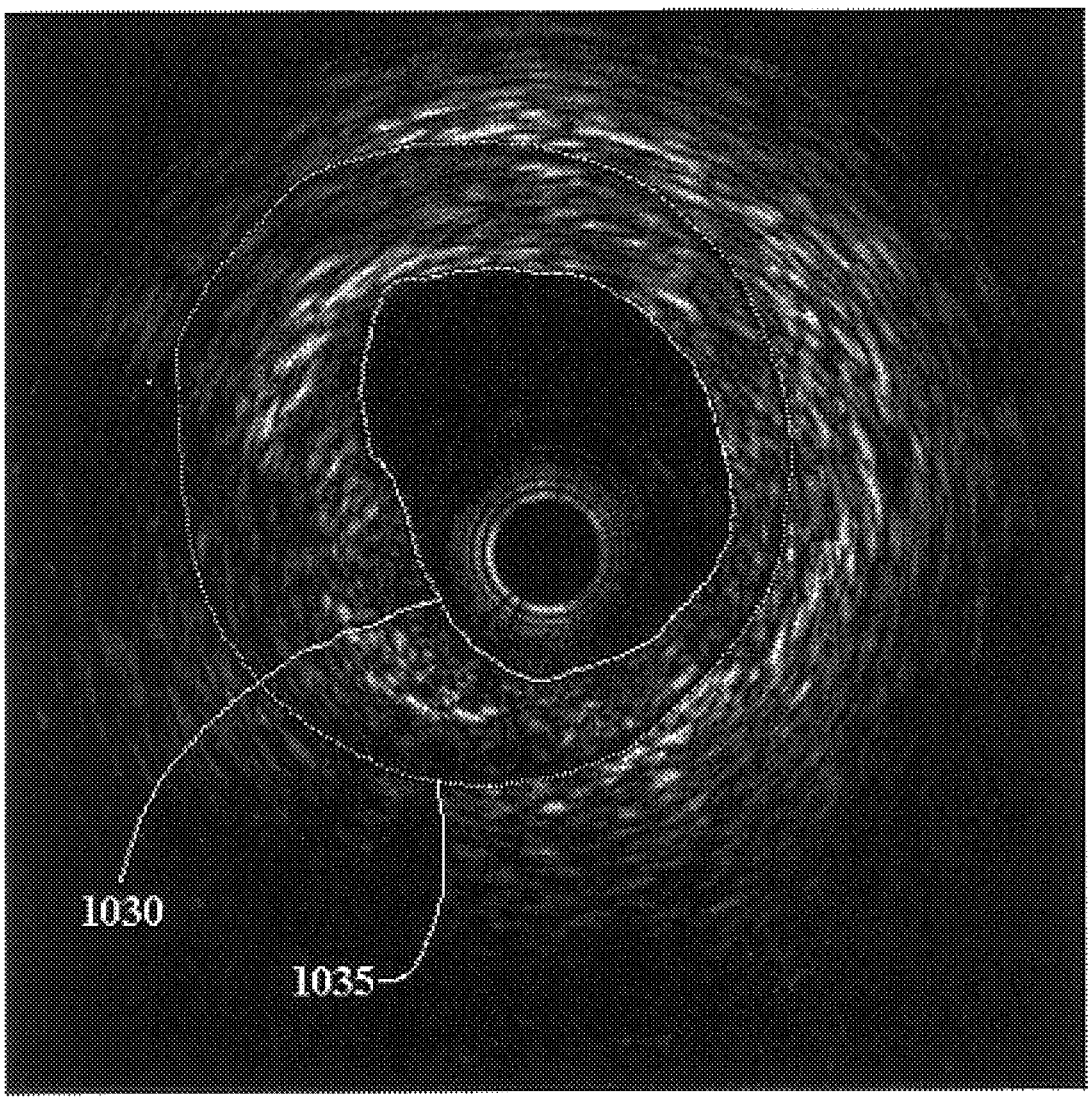
FIG. 15 shows a luminal and medial-advential contours for an image frame.

With reference to FIG. 15, image frame 0 is shown including a luminal contour 1030 and a medial-adventitial contour 1035. To determine the medial-adventitial contour, the process is repeated by selecting control points on the image at locations believed to be in the vicinity of the medial-adventitial boundary of the vessel. Of course, the processing may be performed simultaneously where the user selects boundary control points for both the luminal boundary and medial-adventitial boundary on the selected starting frame and ending frame. Once the medial-adventitial boundary data is found for all frames, plaque analysis can be performed by comparing the luminal boundary contour data and the medial adventitial boundary contour data. By knowing the distance between each frame, as determined by tracking the location of the transducer during image acquisition, volumetric information such as the plaque volume can be calculated.

The invention has been described with reference to the preferred embodiment. Obviously, modifications and alterations to others upon a reading and understanding of this specification. It is intended to include all such modifications and alterations insofar as they come within the scope of the appended claims are the equivalence thereof.

We claim:

1. A method of determining a boundary contour of a blood vessel from an intravascular ultrasound image where the ultrasound image is generated from data acquired radially within the blood vessel by an ultrasonic device, the method comprising the steps of:
    displaying the ultrasound image, the ultrasound image being a cross-sectional view of a blood vessel and being a Cartesian image, the ultrasound image including a representation of a boundary of the blood vessel;
    selecting control points along the boundary of the blood vessel from the Cartesian image;
    interpolating between the control points to generate a boundary contour from the Cartesian image; and
    optimizing the boundary contour from the Cartesian image by adjusting each of the control points based on a gradient polar image which includes a distinguished boundary of the blood vessel, the gradient polar image being determined from the ultrasound image.

2. The method of determining a boundary contour as set forth in claim 1 further including determining the distinguished boundary by radially analyzing pixel values of the ultrasound image.

3. The method of determining a boundary contour as set forth in claim 1 wherein the gradient image is formed by:
    converting the ultrasound image to a polar image, the polar image having a plurality of radial scan lines which include a plurality of pixels;
    radially determining an edge of the boundary along each of the radial scan lines by applying a gradient filter to each of the plurality of pixels, the gradient filter distinguishing pixels which likely form the edge of the boundary, the distinguished pixels defining the distinguished boundary; and
    converting the polar image of the ultrasound image to a Cartesian format to obtain the gradient image in Cartesian format including the distinguished boundary.

4. The method of determining a boundary contour as set forth in claim 1 wherein the optimizing further includes adjusting each of the control points based on a point spacing constraint and a curvature constraint maintain continuity in the boundary contour.

5. The method of determining a boundary contour as set forth in claim 4 further including iteratively performing the optimizing step for each of the control points.

6. The method of determining a boundary contour as set forth in claim 1 wherein:
    the displaying further includes displaying a plurality of ultrasound images being a sequential sequence of images of the blood vessel, the ultrasound image being a starting image;
    the selecting further includes selecting control points along the boundary on an ending image from the plurality of ultrasound images such that at least one intermediate image is between the starting and ending images; and
    the interpolating further includes interpolating between the control points of the starting and ending images to automatically generate a boundary contour on the at least one intermediate image.

7. The method of determining a boundary contour as set forth in claim 6 further including:
    optimizing the boundary contour on the starting image, the at least one intermediate image and the ending image by adjusting each of the control points based on a gradient image which includes a distinguished boundary determined from the ultrasound image of the starting image, the at least one intermediate image and the ending image.

8. A method of intravascular analysis of an intravascular image, the intravascular image being generated from data acquired by an ultrasonic device which radially scans a vascular object internally, the method comprising the steps of:
    converting the intravascular image to a Cartesian format, the intravascular image representing a boundary of the vascular object;
    selecting a plurality of boundary points on the intravascular image in a vicinity of the boundary;
    generating a first boundary contour based on the plurality of boundary points;
    generating a second boundary contour based on a radial boundary determination performed on a polar image of the intravascular image; and
    adjusting the first boundary contour by an influence from the second boundary contour to obtain an optimized boundary contour.

9. The method of intravascular analysis as set forth in claim 8 wherein the generating the first boundary contour includes linearly interpolating between the plurality of boundary points.

10. The method of intravascular analysis as set forth in claim 8 wherein the generating the second boundary contour includes applying a gradient filter to the polar image.

11. The method of intravascular analysis as set forth in claim 10 wherein the radial boundary determination includes applying the gradient filter in a radial direction on the polar image, the gradient filter distinguishing areas of the polar image in the vicinity of the boundary of the vascular object.

12. The method of intravascular analysis as set forth in claim 8 wherein the generating the second boundary contour includes:

converting the intravascular image into the polar image having a plurality of scan lines;

forming a gradient image of the polar image by radially applying a gradient filter across each of the plurality of scan lines to distinguish the boundary of the vascular object; and converting the gradient image to a Cartesian format, the distinguished boundary defining the second boundary contour.

13. The method of intravascular analysis as set forth in claim 8 wherein the adjusting further includes adjusting each of the plurality of boundary points in accordance with a spacing function with restricts a location of a boundary point based on an average distance between each of the plurality of boundary points.

14. The method of intravascular analysis as set forth in claim 13 wherein the adjusting further includes adjusting each of the plurality of boundary points in accordance with a curvature function which restricts a location of a boundary point based on a curvature of the first boundary contour.

15. The method of intravascular analysis as set forth in claim 8 wherein each of the plurality of boundary points has a location on the intravascular image and, the adjusting includes adjusting the location of each of the plurality of boundary points based on a corresponding location on the second boundary contour.

16. The method of intravascular analysis as set forth in claim 8 wherein the boundary is a luminal boundary of the vascular object.

17. The method of intravascular analysis as set forth in claim 8 wherein the boundary is a medial adventitial boundary of the vascular object.

18. A method of intravascular ultrasound image analysis where an intravascular image is generated from ultrasonic data acquired radially from an ultrasonic device from within a vascular object, the improvement comprising:

determining a boundary of the vascular object in accordance with a user defined boundary from image data having a first coordinate format and a polar image of the intravascular image having a second coordinate format different from the first coordinate format.

19. The method as set forth in claim 18 further includes:

applying a gradient to the polar image, the gradient generating a distinguished edge within the polar image which represents the boundary of the vascular object; and adjusting the user defined boundary based on the distinguished edge within the polar image to obtain the boundary of the vascular object.

20. The method as set forth in claim 18 wherein the improvement further includes:

selecting a group of ultrasonic images from the ultrasonic data acquired from a segment of the vascular object, the group of ultrasonic images being defined by a starting image and an ending image which have intermediate images therebetween;

generating a starting boundary contour on the starting image representative of the boundary of the vascular object;

generating an ending boundary contour on the ending image representative of the boundary of the vascular object; and generating a boundary contour on each of the intermediate images representative of the boundary of the vascular object based on the starting and ending boundary contours.

21. The method as set forth in claim 20 wherein the generating a starting and ending boundary contours further includes:

selecting the boundary of the vascular object with a plurality of boundary points on both the starting image and the ending image; and interpolating the plurality of boundary points on the starting image to obtain the starting boundary contour; and interpolating the plurality of boundary points on the ending image to obtain the ending boundary contour.

22. The method as set forth in claim 21 wherein the generating a boundary contour on each of the intermediate images includes interpolating the starting boundary contour and the ending boundary contour across the intermediate images.

23. The method as set forth in claim 22 further including:

generating a corresponding polar image for each of the starting, intermediate and ending images; and adjusting the starting, intermediate and ending boundary contours based on the corresponding polar image.

24. A method of determining a boundary contour of a blood vessel from a series of intravascular ultrasound images which are generated from data acquired radially within the blood vessel by an ultrasonic device, the method comprising the steps of:

selecting a starting image and an ending image from the series of intravascular ultrasound images which define a group of images having intermediate images therebetween;

selecting boundary points on the starting and ending images which are in a vicinity of and partially outline a boundary of the blood vessel;

generating a starting contour outlining the boundary of the blood vessel based on the boundary points of the starting image and generating an ending contour outlining the boundary of the blood vessel based on the boundary points of the ending image;

generating intermediate contours outlining the boundary of the blood vessel for each of the intermediate images based on the starting and ending contours; and determining a boundary contour of the blood vessel in three dimensions based on the starting, intermediate and ending contours.

25. The method of determining a boundary contour of a blood vessel as set forth in claim 24 further including optimizing the starting contour, the intermediate contours, and the ending contour by adjusting each contour based on a polar image generated from the corresponding ultrasound image.

26. The method of determining a boundary contour of a blood vessel as set forth in claim 25 further including adjusting the polar image to distinguish pixel values around a boundary in the polar image.

27. The method as set forth in claim 18 wherein the first coordinate format is in Cartesian coordinates and the second coordinate format is in polar coordinates.

* * * * *